US012611459B2

(12) United States Patent
Yoo et al.

(10) Patent No.: US 12,611,459 B2
(45) Date of Patent: Apr. 28, 2026

(54) SYSTEM AND METHOD FOR UNBINDING OF PLASMA PROTEIN-BOUND ACTIVE AGENTS USING AN ULTRASOUND SYSTEM

(71) Applicant: The Brigham and Women's Hospital, Inc., Boston, MA (US)

(72) Inventors: Seung-Schik Yoo, Wellesley Hills, MA (US); Alexander Rotenberg, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1153 days.

(21) Appl. No.: 17/616,552

(22) PCT Filed: Jun. 5, 2020

(86) PCT No.: PCT/US2020/036335
§ 371 (c)(1),
(2) Date: Dec. 3, 2021

(87) PCT Pub. No.: WO2020/247757
PCT Pub. Date: Dec. 10, 2020

(65) Prior Publication Data
US 2022/0233695 A1     Jul. 28, 2022

Related U.S. Application Data

(60) Provisional application No. 62/857,343, filed on Jun. 5, 2019.

(51) Int. Cl.
*A61K 41/00*     (2020.01)
*A61N 7/00*     (2006.01)
*A61N 7/02*     (2006.01)

(52) U.S. Cl.
CPC ............ *A61K 41/0028* (2013.01); *A61N 7/02* (2013.01); *A61N 2007/0021* (2013.01)

(58) Field of Classification Search
CPC ..................... A61B 2090/378; A61M 37/0092
See application file for complete search history.

(56) References Cited

U.S. PATENT DOCUMENTS

2002/0090738 A1     7/2002   Cozzette et al.
2006/0264809 A1*   11/2006   Hansmann ............. A61B 17/22
                                                                604/22

(Continued)

OTHER PUBLICATIONS

J. Choi et al, "Noninvasive and localized blood-brain barrier disruption using focused ultrasound can be achieved at short pulse lengths and low pulse repetition frequencies", Journal of Cerebral Blood Flow and Metabolism, vol. 31, pp. 725-737, 2011 (Year: 2011).*

(Continued)

*Primary Examiner* — Nyrobi Celestine
(74) *Attorney, Agent, or Firm* — QUARLES & BRADY LLP

(57)     ABSTRACT

An ultrasound system for use in unbinding an active agent from a plasma protein in a target site in a subject includes a transducer configured to generate acoustic pressure waves and a controller coupled to the transducer. The controller is programmed to control the transducer to produce a plurality of pulsed acoustic pressure waves in the target site of the patient. The plurality of pulsed acoustic pressure waves disrupt a plasma protein binding between the active agent and the plasma protein within the target site. The disruption of the plasma protein binding causes an increase in an amount of unbound active agent in the target site.

18 Claims, 5 Drawing Sheets

(56) References Cited

U.S. PATENT DOCUMENTS

| | | | |
|---|---|---|---|
| 2011/0144566 A1 | 6/2011 | Dacey, Jr. et al. | |
| 2011/0208021 A1 | 8/2011 | Goodall et al. | |
| 2012/0174650 A1 | 7/2012 | Ariessohn et al. | |
| 2012/0329082 A1 | 12/2012 | Viola et al. | |
| 2021/0213307 A1* | 7/2021 | Kost | A61N 7/022 |

OTHER PUBLICATIONS

C. Mustafa et al, "Closed-loop cavitation control for focused ultrasound-mediated blood-brain-barrier opening by long-circulating microbubbles", Physics in Medicine and Biology, pp. 1-27, 2018 (Year: 2018).*

H. Kamimura et al, "Feedback control of microbubble cavitation for ultrasound-mediated blood-brain barrier disruption in non-human primates under magnetic resonance guidance", Journal of Cerebral Blood Flow and Metabolism, vol. 39, No. 7, pp. 1191-1203, 2019 (Year: 2019).*

M. Burgess et al, "Power cavitation-guided blood-brain barrier opening with focused ultrasound and microbubbles", Physics in Medicine and Biology, vol. 63, No. 6, p. 1-20, Mar. 2019 (Year: 2019).*

V. Garbin et al, "Unbinding of targeted ultrasound contrast agent microbubbles by secondary acoustic forces", Physics in Medicine and Biology, vol. 56, pp. 6161-6177, Aug. 2011 (Year: 2011).*

"An Overview of the Biological Effects of Focused Ultrasound", Jul. 2015 (Year: 2015).*

International Search Report and Written Opinion of International Application No. PCT/US2020/036335, mailed Aug. 19, 2020, 9 pages.

* cited by examiner

SYSTEM AND METHOD FOR UNBINDING OF PLASMA PROTEIN-BOUND ACTIVE AGENTS USING AN ULTRASOUND SYSTEM

CROSS-REFERENCE TO RELATED APPLICATIONS

This application is based on, claims priority to, and incorporates herein by reference in its entirety U.S. Ser. No. 62/857,343 filed Jun. 5, 2019, and entitled "Systems and Methods for Unbinding of Plasm Protein-Bound Active Agents."

FIELD

The present disclosure relates generally to a system and method for ultrasound and more particularly, to a system and method for unbinding of plasma protein-bound active agents using unfocused or focused ultrasound.

BACKGROUND

Plasmas proteins (PP) play a key role in regulating the pharmacologic activity of active agents (e.g., drugs) in the body. The efficacy and toxicology of an active agent (e.g., drug) are associated with and impacted by the fraction of the drug in the serum (blood) that is unbound to plasma proteins. The PP-bound portion of a drug is sequestered from the effective drug concentration. This process is called plasma protein binding (PPB), and limits the amount of free, unbound, drug-compound available to diffuse out of the blood and exert a desired effect on pharmacologic targets (e.g., receptors, cells), to be metabolized, and to be eliminated. The extent of a drug's PP binding, therefore, influences the way in which a drug distributes into the tissues. PP binding applies to most drugs available.

There are many molecular interactions that determine the degree of drug PP binding (as there are numerous drugs and numerous types of plasma proteins). Among them, acidity and surface charge in conventional solution govern how a drug interacts with the PP. In general, acidic (e.g., aspirin, penicillin and phenytoin) and neutral drugs (e.g., acetaminophen) primarily bind to albumin (most common and abundant PP), and basic drugs (e.g., quinidine, propranolol and amitriptyline) bind to the alpha-1 acid glycoprotein or lipoproteins. The extent of binding is greatly influenced by kinetic and dynamic properties of pharmacological actions of these drugs. For example, an acid and anti-epileptic medication call phenytoin is only ~12% available in an unbound state at clinical dose. Therefore, predicting the interaction of a new drug with the PP is an important technical issue in the pharmaceutical industry, and computer software may be used to model the binding of drug molecules to the PP.

PPB is particularly important for drugs that act on the central nervous system (CNS), as the activity of these drugs is further limited by the blood-brain barrier (BBB). The BBB, formed by astrocyte foot processes and tight junctions between endothelial cells that line the blood vessels of the brain, constitutes a highly selective barrier between systemic blood and the brain/cerebrospinal fluid (CSF). The BBB serves an important protective role for the CNS but also greatly limits effective drug delivery (particularly hydrophilic drugs) to the brain. The drugs that are able to cross the BBB are generally under ~400-500 Da molecular weight (MW) and are able to traverse the barrier via transmembrane diffusion, transporters, endocytosis, or extracellular mechanisms.

PPB is mediated by electrostatic (hydrogen-bonds) or van der Waal's interactions (and mutual forces) between the drugs and PP are considered as the main sources of attraction between PP and the drug. Such interactions are rapid, weak (on the order of pico newtons, $10^{-12}$ N) and reversible, as is necessary for effective drug delivery to target. Alteration of the binding can occur when PP serum concentration varies physiologically (during pregnancy) or due to the pathologic conditions (such as renal or liver disease).

Intentional adjustment for more unbound, free drugs in the serum has been achieved by either binding displacement (i.e., concomitant introduction of multiple drugs, modifying the binding interactions, e.g., phenytoin or warfarin or simple increase in initial intake of drug (to increase the serum level of the drug)); however, these processes are accompanied by the risk of increased toxicity or burden for the metabolic process of the combination/elevated level of drugs. In addition, these processes take place systematically in the blood, not in the spatially-localized regions as would be highly desirable to deliver anatomically-targeted therapy while mitigating risk of systemic toxicity. Therefore, research and medical communities have sought after a means for spatially-selective drug unbinding from PP.

It would be desirable to provide a system and method to unbind a drug (or active agent) from plasma protein in a region of interest to increase a local concentration of the drug in the region of interest and reduce the risk of systemic toxicity.

SUMMARY

In accordance with an embodiment, an ultrasound system for use in unbinding an active agent from a plasma protein in a target site in a subject includes a transducer configured to generate acoustic pressure waves and a controller coupled to the transducer. The controller is programmed to control the transducer to produce a plurality of pulsed acoustic pressure waves in the target site of the patient. The plurality of pulsed acoustic pressure waves disrupt a plasma protein binding between the active agent and the plasma protein within the target site. The disruption of the plasma protein binding causes an increase in an amount of unbound active agent in the target site.

In accordance with another embodiment, a method for unbinding an active agent from a plasma protein in a target site in a subject using an ultrasound system having a transducer and a controller includes determining, using the controller, a set of parameters for a plurality of pulsed acoustic pressure waves and generating, using the transducer, the plurality of pulsed acoustic pressure waves in the target site of the patient. The plurality of pulsed acoustic pressure waves disrupt a plasma protein binding between the active agent and the plasma protein within the target site. The disruption of the plasma protein binding causes an increase in an amount of unbound active agent in the target site.

BRIEF DESCRIPTION OF THE DRAWINGS

The present disclosure will hereafter be described with reference to the accompanying drawings, wherein like reference numerals denote like elements.

DETAILED DESCRIPTION

Figure 1:
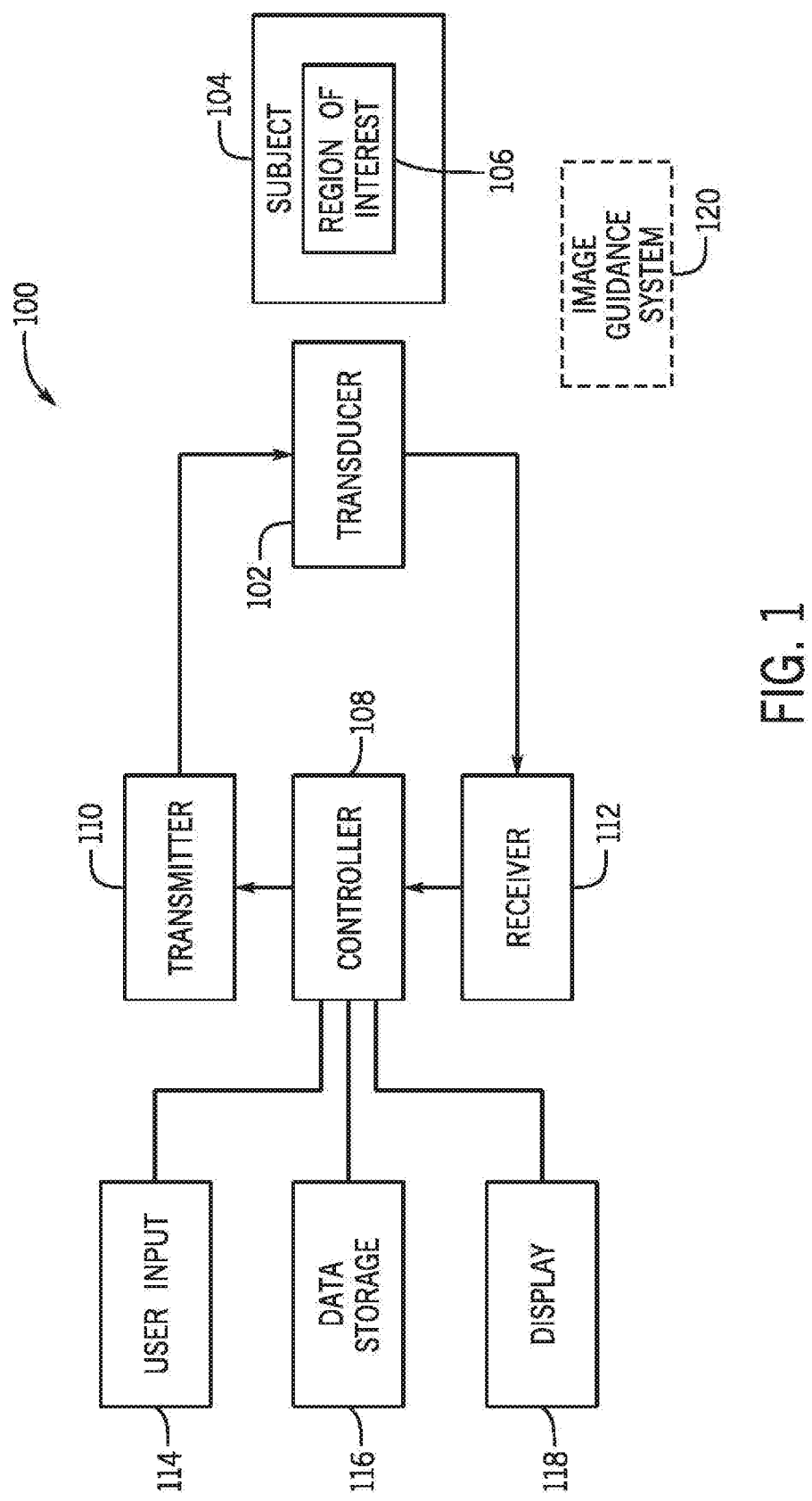
FIG. 1 is a block diagram of an example ultrasound system in accordance with an embodiment.

Unless otherwise defined, all technical and scientific terms used herein have the same meaning as commonly understood by one of ordinary skill in the art to which this invention belongs. In case of conflict, the present application, including definitions will control.

As used herein, the term "focused ultrasound" refers to non-ionizing, mechanical energy in a form of acoustic pressure waves specifically directed to a target site.

As used herein, the term "target site" refers to a location or a site within the body where focused ultrasound is applied, such that the mechanical energy of the ultrasound is directed to, and can reach the site.

As used herein, the term "active agent" (e.g., drug) refers to any chemical or biological agent that affects the structure or any function of the body. An active agent is typically intended for use in the diagnosis, cure, mitigation, treatment, or prevention of disease.

As used herein, the term "plasma protein" refers to proteins present in the blood plasma, typically produced by the liver. Most commonly, the plasma protein of interest is albumin or alpha-1 acid glycoprotein.

As used herein, "an increase in active agent" refers to an increase that is at least about 0.05 fold more (for example, about 0.1, 0.2, 0.3, 0.4, 0.5, 1, 5, 10, 25, 50, 100, 1000, 10,000-fold or more) than in a subject not undergoing focused ultrasound according to the methods described herein. An "an increase in active agent" can also refer to at least about 5% more (for example about 5, 6, 7, 8, 9, 10, 15, 20, 25, 30, 35, 40, 45, 50, 55, 60, 65, 70, 75, 80, 85, 90, 95, 99 or 100%) than in a subject not undergoing focused ultrasound according to the methods described herein. Amounts can be measured according to methods known in the art for measuring active agents in the blood.

Unless specifically stated or clear from the context, as used herein, the term "about" is understood as within a range of normal tolerance in the art, for example, within 2 standard deviations of the mean. "About" is understood as within 10%, 9%, 7%, 6%, 5%, 4%, 3%, 2%, 1%, 0.5%, 0.1%, 0.05%, or 0.01% of the stated value. Unless otherwise clear from the context, all numerical values provided herein are modified by the term about.

As used herein, the term "reference level" refers to the level of active agent in a known sample against which another test sample is compared. A reference level can be obtained, for example, from a known sample from a different individual (e.g., not the individual being tested), not having undergone focused ultrasound. The reference level may be determined before and/or after treatment and optionally, from samples obtained from the same subject before and/or treatment. A known sample can also be obtained by pooling samples from a plurality of individuals to produce a reference level over an averaged population.

As used herein, a "sequence" refers to a sonication protocol having features including insonification pulse, duration, number of insonification pulses, inter-insonification pulse intervals and amplitude.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

The present disclosure describes a system and method for providing spatially-localized unbinding of active agents from plasma proteins, thereby enhancing the level of unbound active agents at a target site and increasing the level of active agent. In particular, focused or unfocused ultrasound (U/S) is used to facilitate mechanical separation of the active agent from the binding plasma protein by providing acoustic pressure waves into a specific region of interest or target site in a subject. The acoustic pressure waves provide a sustained mechanical force that is sufficient to overcome the binding forces involved in plasma protein binding (PPB) leading to unbinding of the active agent from plasma proteins and a rise in the local concentration of unbound active agent within the blood, thus locally enhancing the concentration of free active agents within, for example, the tissue at the target site. Accordingly, the described system and method provides a focused or unfocused ultrasound mediated non-invasive unbinding of plasma protein-bound active agents. The system and method may be used to change local pharmacokinetics and pharmacodynamics. By increasing or enhancing the local concentration of an unbound active agent, systemic toxicity may be mitigated while delivering a therapeutic concentration of free (unbound to protein) active agent to a specific tissue or organ. In other words, the disclosed system and method may be used to deliver regional levels of an active agent to a region of interest (or target site) without adversely affecting other regions or organs. In an embodiment, the acoustic pressure waves may be delivered using focused ultrasound techniques. In another embodiment, if the region of interest does not require spatial selectivity or deep tissue penetration (e.g., skin, skull, or muscle) the acoustic pressure waves may be delivered in an unfocused manner.

In various embodiments, the system and method for unbinding of plasma protein-bound active agents using an ultrasound system may be used on a non-trans-osseous target site, e.g., muscles or body tissue whereby the ultrasound can reach the tissue without passing through the bone. Accordingly, methods disclosed herein may be applied to ameliorate symptoms or modify disease in extracranial targets. In these embodiments, protein binding and disloca-tion of drug from plasma protein is essential for drug efficacy, but blood brain barrier penetration is not relevant. In specific embodiments, categories of disease, syndrome, symptom or medical condition include, but are not limited to joint pain and/or inflammation, as occurs in osteoarthritis, rheumatoid arthritis and gout, wherein, for example, ibu-profen or naproxen are administered. Ultrasound (focal or non-focal) can be applied over the affected joint to promote local concentration of an anti-inflammatory agent.

In another embodiment, Ultrasound can be applied to malignancy (primary tumor or metastatic tumor) affecting skin, muscle, bone, liver, testes or other organs, wherein, for example, cisplatin or vincristine are administered. Ultrasound can be applied over the tumor to promote local concentration of chemotherapeutic agent.

In another embodiment, Ultrasound can be applied to peripheral neuropathies impacting the spinal cord and dorsal root ganglia, such as shingles, wherein, for example, lidocaine and bupivacaine are administered.

In other embodiments, the system and method for unbinding of plasma protein-bound active agents using focused ultrasound may be used on a trans-osseous/transcranial target site, e.g., muscles or body tissue whereby the ultrasound can reach the tissue through the bone. In specific embodiments, systems and methods of the invention are provided to transcranial locations associated with diseases of the central nervous system. The epileptogenic zone or seizure propagation zone in the neocortex or hippocampus is targeted when active agents are administered for the treatment of focal epilepsy. The thalamus or another deep nucleus is targeted when active agents are administered for the treatment of primary generalized epilepsy. The prefrontal cortex, cingulate gyms, insula, basal ganglia is targeted when the active agents are administered for the treatment of major depression. Neocortical areas in the frontal, parietal and temporal lobe are targeted when active agents are administered for the treatment of schizophrenia. Deep brain areas such as the globus palidus and subthalamic nucleus are targeted when active agents are administered for the treatment of Parkinson's disease. The prefrontal cortex is targeted when active agents are administered for the treatment of attention deficit disorder. Sensorimotor areas in precentral, central, and postcentral gyri, and the spinal cord are targeted when active agents are administered for the treatment of amyotrophic lateral sclerosis. Depending on the location of the target site, the disclosed system may be adjusted to focus the ultrasound as needed by one of skill in the art.

In an embodiment, the disclosed systems and methods may be used to improve drug delivery across the blood brain barrier (BBB) by increasing the local level of the unbound drug available to cross the BBB. The unbound active agents pass through the BBB via passive diffusion or a physiological transport mechanism, all without actively disrupting the BBB.

In an embodiment, the pressure waves of the ultrasound (focused and unfocused) are administered at an intensity below the limit that can induce a temperature change at the target site (i.e. the mechanism of action is non-thermal). Temperature elevation is not desirable since it could alter not only the local blood perfusion, but also can irreversibly damage the tissue/cells die to heat damage. To do so, ultrasound pressure waves are administered in an amount and sequence sufficient to disrupt the complex formed between the active agent and the plasma protein by pulsing the ultrasound in intervals that maintain the tissue temperature at the target site. For example, a 55 ms pulse duration of ultrasound given every 250 msec interval (i.e. duty cycle of 22%) at an acoustic intensity of 5 W/cn$^2$ spatial-peak-pulsed-averaged intensity ($I_{sppa}$) can dissociate the plasma bound protein complex without thermal damage at the target site. Depending on the type of active agent (and its binding force to the plasma protein), the acoustic pressure can be adjusted by one of skill in the art to provide an increase or decrease in pressure.

The active agents that are targeted by the disclosed systems and methods may be selected based on the following criteria: molecular weight, type of acidity and percent of binding to plasma proteins. In an embodiment, the targeted active agents may include, but are not limited to, those with a small molecular weight, an acidic or basic type of acidity, and 70% affinity (binding). In another embodiment, for applications involving regions of the brain the active agents that are targeted by the disclosed systems and methods may include, but are not limited to those meeting the following criteria: 1) active agents having activity in the central nervous system, (2) high PPB ratio (more than 80%), and (3) molecular weights of less than 400 g/mol (which is small enough to pass through the BBB without disrupting BBB). In various embodiments, active agents are Antidepressants including bupropion, fluoxetine, mirazapine, vortioxetine; Immune modjlators including fingolimod; Anxiolytics including alprazolam, diazepam, lorazepam; Antipsychotics including olanzapine; Sodium channel blockers (e.g., for amyotrophic lateral sclerosis) including riluzole; cholinergics (e.g., for Alzheimer's disease) including donepezil; catechol-O-methyltransferase inhibitors (e.g., for Parkinson's disease) including entacapone; monoamine oxidase-B inhibitors (e.g., for Parkinson's disease) including rasagiline; norepinephrine reutake inhibitors (e.g., for attention deficit disorder) including atomoxetine; antiepileptics including phenytoin.

Ultrasound pressure waves, if not focused, propagate through the media in a non-focal manner. They can also be delivered to a small, localized, biological tissue. This approach, called focused ultrasound (FUS), has been applied in various therapeutic approaches, including thermal ablation of the tumors in body. Various approaches, using single- and multi-element transducer configurations under image-guidance, have been taken to generate and place a small acoustic focus to a deep brain area with great spatial specificity (the focus is approximately the size of Orzo pasta or a rice grain, depending on the hardware used) and accuracy. The technique, called transcranial FUS (tFUS), has shown initial utility in thermal ablation (when given in high acoustic intensity) and non-thermal (via low-intensity administration below the threshold to cause the temperature elevation) stimulation of the brain tissue.

Referring now to FIG. 1, the disclosed systems and methods may be implemented using an ultrasound system, such as the example ultrasound system 100 illustrated in FIG. 1. Ultrasound system 100 may be configured to perform deliver focused ultrasound ("FUS") or unfocused ultrasound. The ultrasound system 100 generally includes a transducer 102 that is capable of delivering ultrasound to a subject 104 and receiving responsive signal therefrom. Transducer 102 may be a single-element transducer or an arrayed transducer. The transducer 102 may be configured to be a shape and size appropriate for delivering ultrasound energy (focused or unfocused) to a desired region of interest 106 (e.g., a particular tissue or organ) in the subject 104. For example, for brain applications the transducer 102 may be an approximately hemispherical array of transducer elements or a single-element transducer configured to surround a portion of the subjects head.

The ultrasound system 100 also includes a controller (or processor) 108 that is in communication with a transmitter 110 and a receiver 112. The transmitter 110 receives driving signals from the controller 108 and, in turn, directs the transducer elements of the transducer 102 to generate ultrasound energy (or acoustic pressure waves). In an embodiment, the transmitter may include a power amplifier (not shown) and impedance matching circuit (not shown) to amplify signals before transmitting them to the transducer 102. The acoustic pressure waves generated by the transducer 102 are delivered to the region of interest 106 (or target site) via acoustic coupling between the transducer 102 and the subject using various media such as, for example, water or hydrogel. The acoustic intensity (i.e., the acoustic power per given area ($W/cm^2$) is expressed in spatial-peal pulse-average intensity ($I_{sppa}$) while $I_{spta}$ represents its time-average value per each stimulus. In an embodiment, the focused ultrasound delivered by transducer 102 may be given in a batch of pulsed sinusoidal or square pressure waves at a fundamental frequency (FF). The individual pulses each have a specific toe-burst duration (TBD) and are administered in a repeated fashion with a pulse repetition frequency (PRF). The duty cycle of sonication (in %) may be determined by multiplying the TBD by the PRF. The duty cycle indicates the fraction of active sonication time per each sonication. The overall duration of the pulsed sonication is termed sonication duration.

The receiver 112 receives acoustic signals during and/or after sonication and relays these signals to the controller 108 for processing. The controller 108 may also be configured to adjust the driving signals in response to the acoustic emissions recorded by the receiver 112. For example, the phase and/or amplitude of the driving signals may be adjusted so that ultrasound energy is more efficiently transmitted through, for example, the skin and/or the skull of the subject 104 and into the target region of interest (or target site) 106. Furthermore, the acoustic signals may also be analyzed to determine whether and how the extent of the focal region should be adjusted. In an embodiment, an image guided system 120 may be used to navigate the acoustic focus to the region of interest 106. The image guided system 120 may be, for example, MR, fMRI or computer tomography (CT). The image guided system 120 may be co-registered with the physical space using known methods. In another embodiment, numerical acoustic simulation may be used to estimate the location and intensity of the acoustic focus.

Ultrasound system 100 may also include a user input 114, data storage 116 and a display 118 which are coupled to the controller 108. User input 114 may include one or more input devices (such as a keyboard and a mouse, or the like) configured for operation of the controller 108, including the ability for selecting, entering or otherwise specific parameters consistent with performing tasks, processing data, or operating the ultrasound system 100. Data storage 116 may contain software and data and may be configured for storage and retrieval of processed information, instructions, and data to be processed. Display 118 may be used to display, for example, data and images.

Figure 2:
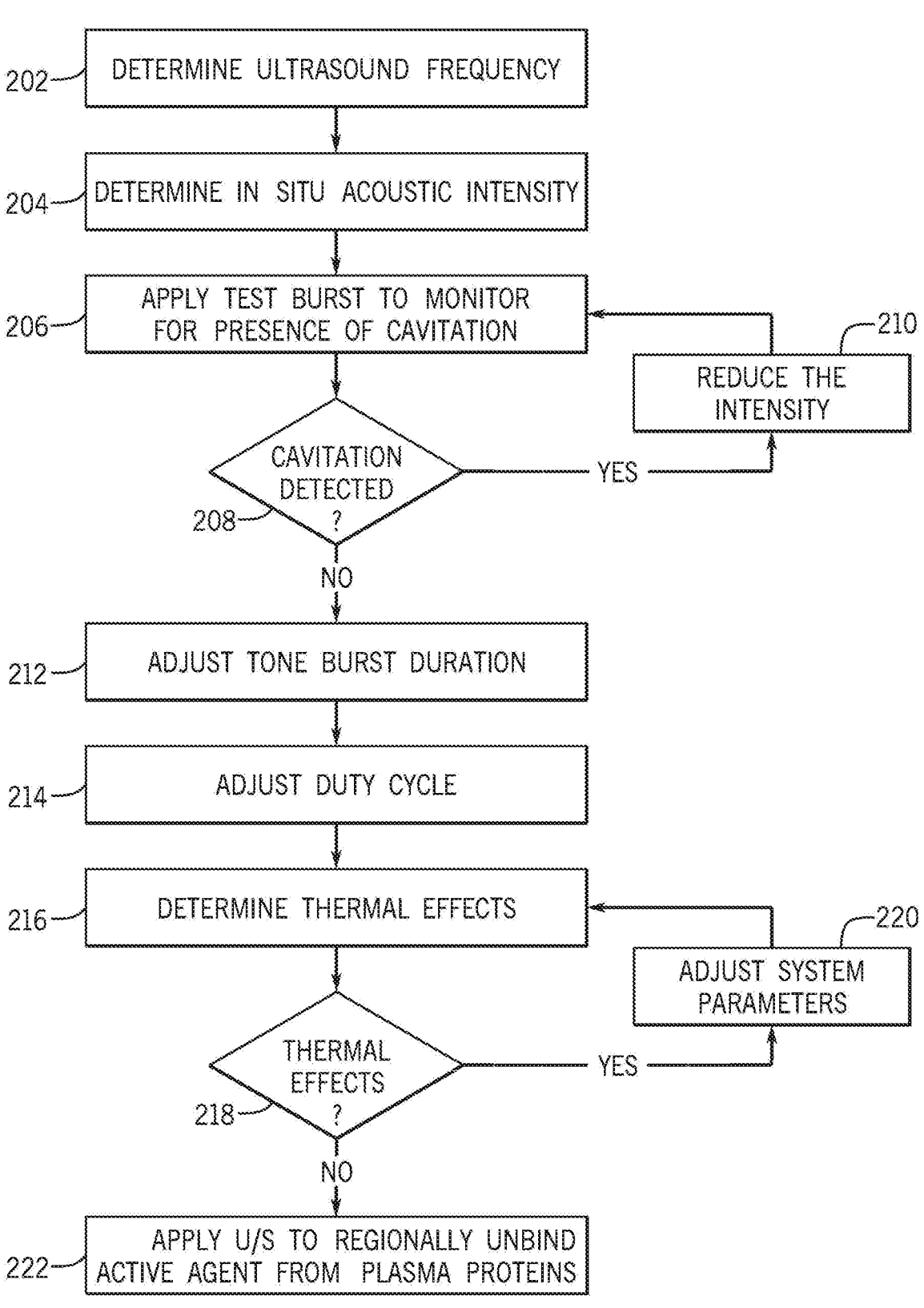
FIG. 2 illustrates a method for unbinding of plasma protein-bound active agents using an ultrasound system.

FIG. 2 illustrates a method for unbinding of plasma protein-bound active agents using an ultrasound system. At block 202, the ultrasound frequency is determined for transmission of the acoustic pressure wave. The ultrasound frequency is selected based on the type of target site or region of interest) for sonication, for example, a non-trans-osseous target site or a trans-osseous/transcranial target site. Osseous biological structures absorb, scatter, and reflect ultrasound waves. In order to transmit ultrasound waves through, for example, the skull, 100 kHz-750 kHz frequency ranges are typically used. For other non-trans-osseous applications, a frequency higher than the above range may be used.

At block 204, the in situ acoustic intensity (and associated acoustic pressure) is determined. In an embodiment, the in situ acoustic intensity and associated acoustic pressure that yield the Mechanical Index (MI)≤1.9 are determined. The mechanical index (MI) is a measure of the likelihood of non-thermal, mechanical bioeffects of ultrasound, including cavitation. As used herein, 'cavitation' refers to the phenomenon of expansion/contraction or collapse of bubbles inside biological tissue due to the applied acoustic pressure of the ultrasound. In an embodiment, the in situ acoustic intensity (i.e. intensity after transmission through, for example, the skull) may be estimated by applying a 'derating factor' (i.e. the level of attenuation of ultrasound pressure caused by the biological tissue in its pathway at the given ultrasound setting, including its frequency and transducer configuration). The MI is defined as the peak negative pressure ($P_r$, in MPa) divided by the square root of the frequency (in MHz) of the ultrasound wave. For clinical ultrasound imaging of organs in the absence of gas-bodies, an MI up to 1.9 is allowed (per the FDA).

At block 206, a plurality of test bursts are applied to (or delivered to) the target site using, for example, an ultrasound system (e.g., ultrasound system 100 shown in FIG. 1). In addition to the estimation of the pressure level, actual validation on the absence of cavitation event is desired. After determining an initial intensity at block 204, test ultrasound waves (short bursts) are delivered a plurality of times to a targeted region of interest (target site) to monitor for the presence of cavitation. In one embodiment where the target site is in the brain, short bursts of ~100 ms long, may be delivered about 10 times to the targeted brain area to monitor for the presence of cavitation. Cavitation-related emissions from the region of interest are detected (e.g., using receiver 112 shown in FIG. 1) in a frequency range much higher than the applied ultrasound frequency. In an embodiment where the target site is in the brain, the frequency range of the cavitation related emissions may be 1-10 $MHz^3$. To detect any cavitation event, a broadband ultrasound transducer (0.5 MHz) may be used as a sensor that is positioned over the region of interest (e.g., over the head). Cavitation-related events (presence of resonant frequency peaks other than sonication frequency) may be detected using a real-time spectrum analyzer using methods known in art.

At block 208, if any cavitation is detected, the process moves to block 210. At block 210, the acoustic intensity is reduced and the process moves to block 206 to determine if there is cavitation present. At block 208, if cavitation is not present the process moves to block 212. After determining the optimal acoustic intensity that will have maximal pressure waves under the threshold for cavitation (blocks 206-210), pulsing parameters are determined. At block 212, first a tone burst duration (TBD) is adjusted to a value in a predetermined range. For example, the TBD may be adjusted to a value in the range of 51-210 ms. At block 214, the duty cycle is then adjusted to a value in a predetermined range. For example, the duty cycle may be adjusted to a value in a 21-100% range. Duty cycle refers to the percentage of time that the sonication is turned on per given second (e.g. if TBD is 100 ms and the sonication is given three times per second –3 Hz, the duty cycle is 30%). In an embodiment, the duty cycle may be changed by changing the pulse repetition frequency (PRF).

At block 216, it is determined whether there are thermal effects of the sonication by, for example, estimating the in situ acoustic intensity or measuring temperature non-invasively. Thermal effects should be considered and avoided. Too much sonication results in energy absorption (and its conversion to heat energy), and may damage the sonicated tissue or may confound the drug-plasma protein unbinding. To do so, in one embodiment effective power deposition, characterized by spatial-peak temporal-average intensity ($I_{spta}$), is estimated, whereby, $I_{spta}$~spatial-peak pulse-average intensity ($I_{sppa}$)×duty cycle. The estimated value can be used for numerical simulation to examine whether there is any temperature elevation. Also, MR thermometry, which is completely non-invasive, may be used to actually measure the temperature of the tissue while sonication is given. At block 218, if any temperature elevation is anticipated or detected, the process moves to block 220. At block 220, acoustic parameters of the ultrasound system, such as, for example, TBD, PRF, and duty cycle may be adjusted and the process returns to block 216. Iterations of blocks 216-220 continue until no thermal effect is present. If there is no thermal effect present at block 218, the process moves to block 222.

At block 222, ultrasound (focused or unfocused) is applied to the region of interest (or target site) to unbind active agent from plasma proteins. In particular, if the sonication can be given under the threshold for (1) cavitation and (2) temperature elevation for normal physiology (less than ~0.5° C. from the baseline), the sonication will be given to the region-of-interest (ROI) for at least a predetermined time to unbind the drug from the plasma proteins. In one embodiment, the sonication is given to the region of interest for five minutes.

In one embodiment, regarding sonication of a non-transosseous target site, guidelines for providing ultrasound in amount and sequence sufficient to disrupt the complex formed between the active agent and the plasma protein may be as follows: (1) frequency of about 20 kHz to about 5 MHz, (2) tone burst duration of about 51 to about 210 ms, (3) duty cycles (tone burst duration×pulse repetition frequency) ranging from about 21% to about 100% (100% is continuous sonication), (3) acoustic pressure level applicable to FDA regulations under the mechanical index (MI)<1.9 (MI is defined as peak negative pressure on $MPa \div \sqrt{}$ frequency in MHz), and total sonication duration adjusted so that the temperature change of the tissue is kept under the 0.1° C.

In another embodiment, regarding sonication of a transosseous/transcranial target site, guidelines for providing ultrasound in an amount and sequence sufficient to disrupt the complex formed between the active agent and the plasma protein may be as follows: (1) frequency of about 20 kHz to about 1 MHz, (2) tone burst duration of about 51 to about 210 ms, (3) duty cycles (tone burst duration×pulse repetition frequency) ranging from about 21% to about 100% (100% is continuous sonication), (4) acoustic pressure level applicable to FDA regulations under the MI<1.9, and (5) total sonication duration adjusted so that the temperature change of the tissue is kept under the 0.1° C.

The following examples set forth, in detail, ways in which the present disclosure was evaluated and ways in which the present disclosure may be used or implemented, and will enable one of ordinary skill in the art to more readily understand the principles thereof. The following examples are presented by way of illustration and are not meant to be limiting in any way.

Example 1

While the following examples describe the active agent phenytoin and the plasma protein albumin, it should be understood that the system and method for unbinding of plasma protein-bound active agents may be applied to a wide range of drug-plasma protein interactions as described above. In this example the effects of focused ultrasound (FUS) on unbinding phenytoin from albumin was evaluated. In particular, sonication by low-intensity focused ultrasound waves was evaluated to determine whether the process can unbind a typical albumin-drug (phenytoin) from the serum albumin in a spatially-restricted fashion, thus locally increasing the availability of free drugs for the potential enhancement of therapeutic effects. Phenytoin is one of the most common drugs for the treatment of epilepsy as a voltage-sensitive sodium channel blocker, and has a high affinity to plasma proteins with an approximately 90% binding level, primarily to albumin.

Albumin (molecular weight ~66 kDa) is a plasma protein abundant in serum that serves many key physiological processes, such as regulations of osmotic pressure and transportation of endogenous materials (e.g., hormones and organic and non-organic metabolites). Albumin account for more than 50% of all plasma proteins. The structural revelation of the detailed molecular structure of human serum albumin (HSA) has shown numerous potential binding sites, and therefore, high affinity to many drugs, especially to the "acidic" drugs (e.g., phenytoin, lorazepam, and valproic acid).

The ability of FUS to unbind phenytoin from albumin was assessed in this example by an equilibrium dialysis (ED), whereby the cocktail of albumin-phenytoin was sonicated, and unbound phenytoin was allowed to pass through the membrane to be collected and analyzed. As a part of in vitro testing, a visible dye, Toluidine Blue O, was dissolved in an aqueous solution of albumin and the spatial distribution of the degree of its unbinding from the albumin through the application of FUS was qualitatively evaluated via gel infiltration using agar gel block.

In this example, an in vitro experimental chamber was constructed using a 3D printer (clear resin) to measure the effects of FUS on albumin-phenytoin binding. The chamber includes four slots to place four microdialysis cassettes (7 kMW cut-off pore size; 4×4×0.8 cm; H×L×W) whereby one is placed perpendicular to the sonication focus ('FF'), and three others are placed away from the focus ('F01' through 'F03'). A FUS transducer having 13 mm focal length (away from the exit plane) and operating at a fundamental frequency of 250 kHz was used to sonicate the middle of the dialysis window ('FF'). The output pressure wave from the transducer was calibrated for the input signal generator and the acoustic map perpendicular to the sonication axis was mapped using known methods. An identical setup was prepared separately and was not sonicated to provide a control.

In this example, bovine serum albumin (BSA) was dissolved in a phosphate-buffered saline (PBS) (pH7.4) at a concentration of 46 mg/mL concentration, and 200 mL of resulting solution was poured into the chamber. The experiment was conducted at a room temperature (20-21° C.) and the solution temperature was equilibrated at the ambient temperature. The solution was not degassed and kept the ambient gas content ($O_2$ 6.1 ppm; measured using dissolved oxygen meter). The wall of the chamber was padded with rubber inserts to absorb the incident acoustic waves to prevent reflection or reverberation within the chamber.

In this example, phenytoin was dissolved (15 µg/mL) in PBS having bovine serum albumin (BSA) concentration of 45 mg/mL to emulate the clinical serum concentration. The temperature of the solution was monitored during the sonication to examine the potential effect from the temperature of the solution on the bound phenytoin. The dialysis cassettes, after hydration according to known methods, were filled with PBS (0.5 ML) and were placed into the bath. Subsequently, sonication was given for 55 min at 250 kHz in pulsed manner (55 ms TBD, 4 Hz PRF, at 5 W/cm2 $I_{sppa}$ Spatial-Peak Pulse-Average Intensity, i.e. 22% duty cycle). The mechanical index (MI) of the focus was 0.8 (corresponding to peak negative pressure of 391 kPa). The temperature of the solution was monitored. Upon the sonication, the dialysis PBS that contains diffused unbound phenytoin was recovered according to the vendor suggestion, and subjected to the further analysis. The obtained samples underwent High Performance Liquid Chromatography (HPLC) for the measurement of phenytoin concentration after the calibration of the known absolute level of the phenytoin. The HPLC system consisted of an autosampler, a dual piston pump, and an electrochemical detector coupled to a guard cell and an analytical cell.

Figure 3:
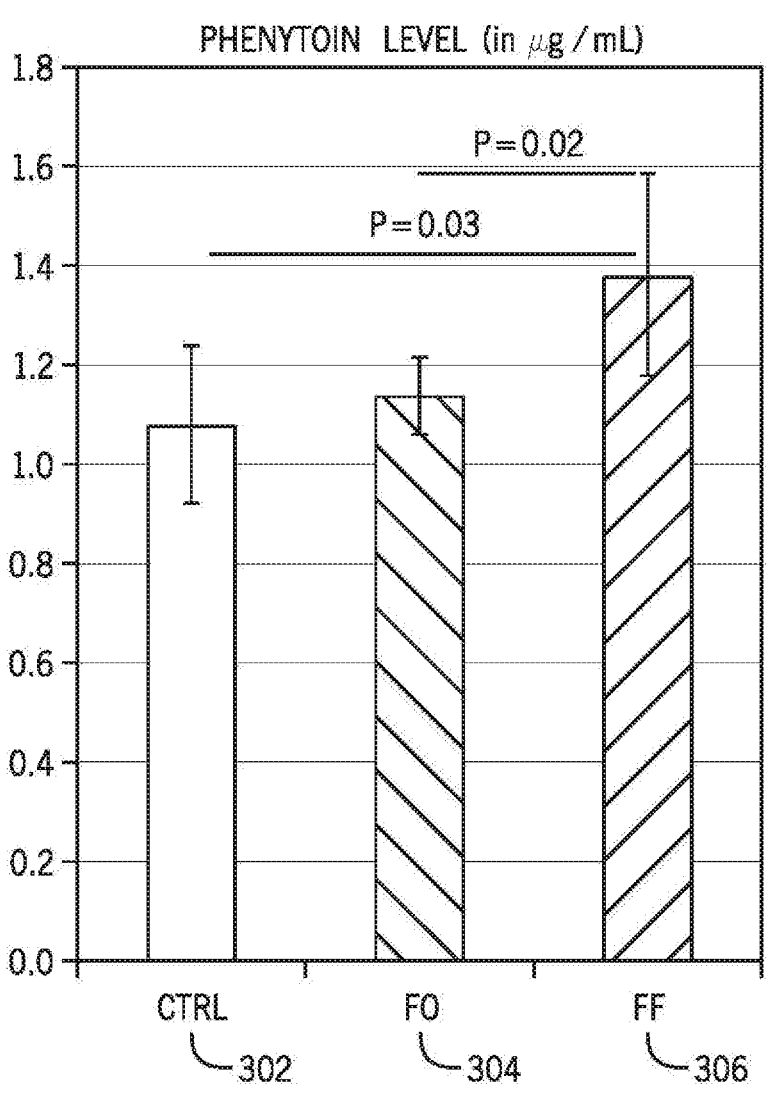
FIG. 3 is an example plot showing a comparison of a measured phenytoin level after sonication in accordance with an embodiment.

FIG. 3 is an example plot showing a comparison of a measured phenytoin level after sonication in accordance with an embodiment. The plot 300 shows a comparison of measured phenytoin level from the control condition 302 ('CTRL'), outside the focus 304 ('FO') and on the focus 306 ('FF'). The averaged phenytoin level 302 from the control chamber in this example was $1.52\pm0.16$ µg/mL (n=12), while the phenytoin level measured from albumin-containing chamber were $1.13\pm0.08$ µg/mL (n=12) at the outside of focus (FO) 304 and $1.38\pm0.2$ (n=6) at the acoustic focus (FF) 306. The unbound phenytoin level at the focus 306 was elevated approximately 27.7% and 21.4% compared to the control and outside of focus, respectively (with $p<0.05$, t-test, one-tail). There was no significant difference in the phenytoin level between the samples acquired from the control condition and outside of focus ($p>0.1$). The temperature of the bath did not change during the course of the experiment.

Example 2

In this example the effects of focused ultrasound (FUS) on unbinding phenytoin from albumin was evaluated in an animal model (rat). The enhancement of phenytoin was assessed using immunohistochemistry (IHC) followed by intraperitoneal injection of phenytoin and subsequent sonication of the unilateral hemisphere. All IHC was performed on an automated staining platform. Hematoxylin and eosin (H&E) staining was also performed to assess for tissue hemorrhage. The same sonication parameters and device were used as in the first example described above except the sonication was delivered for 35 minutes.

Figure 4:
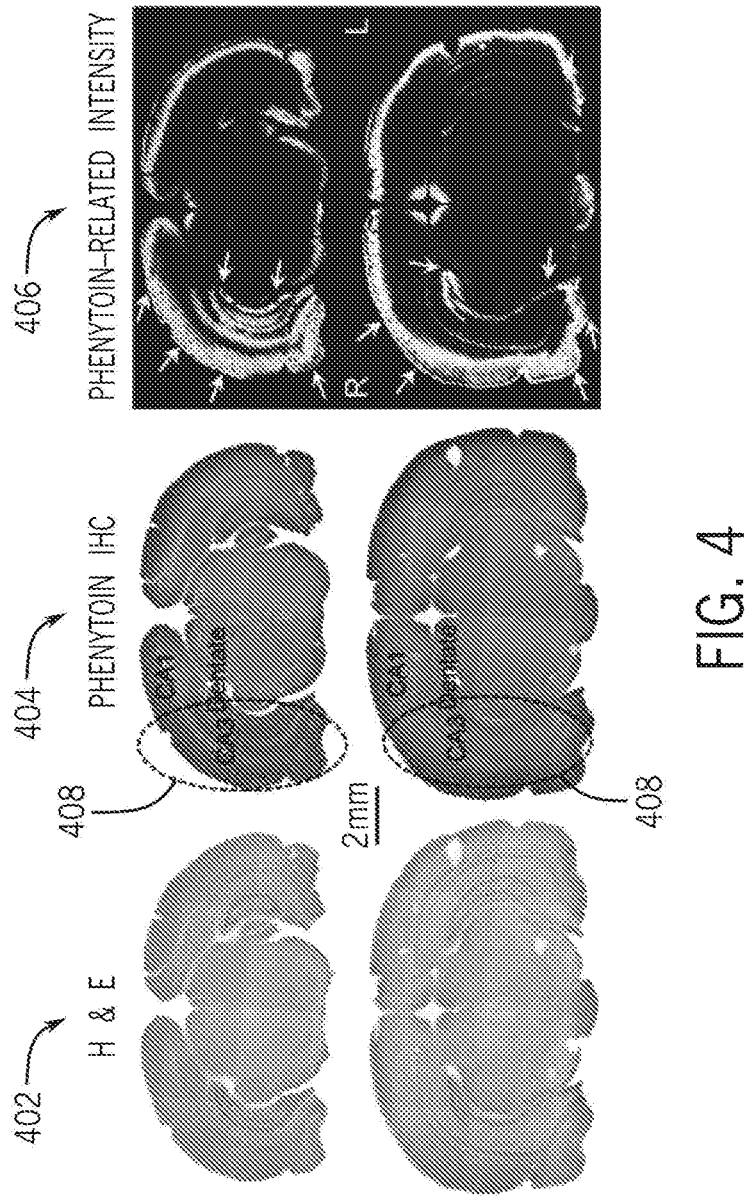
FIG. 4 illustrates example mosaic H&E microscope images, example mosaic phenytoin-stained immunohisto-chemistry (IHC) images and example inverted grayscale images of the phenytoin IHC of sonicated and unsonicated brain regions in accordance with an embodiment.
Figure 5:
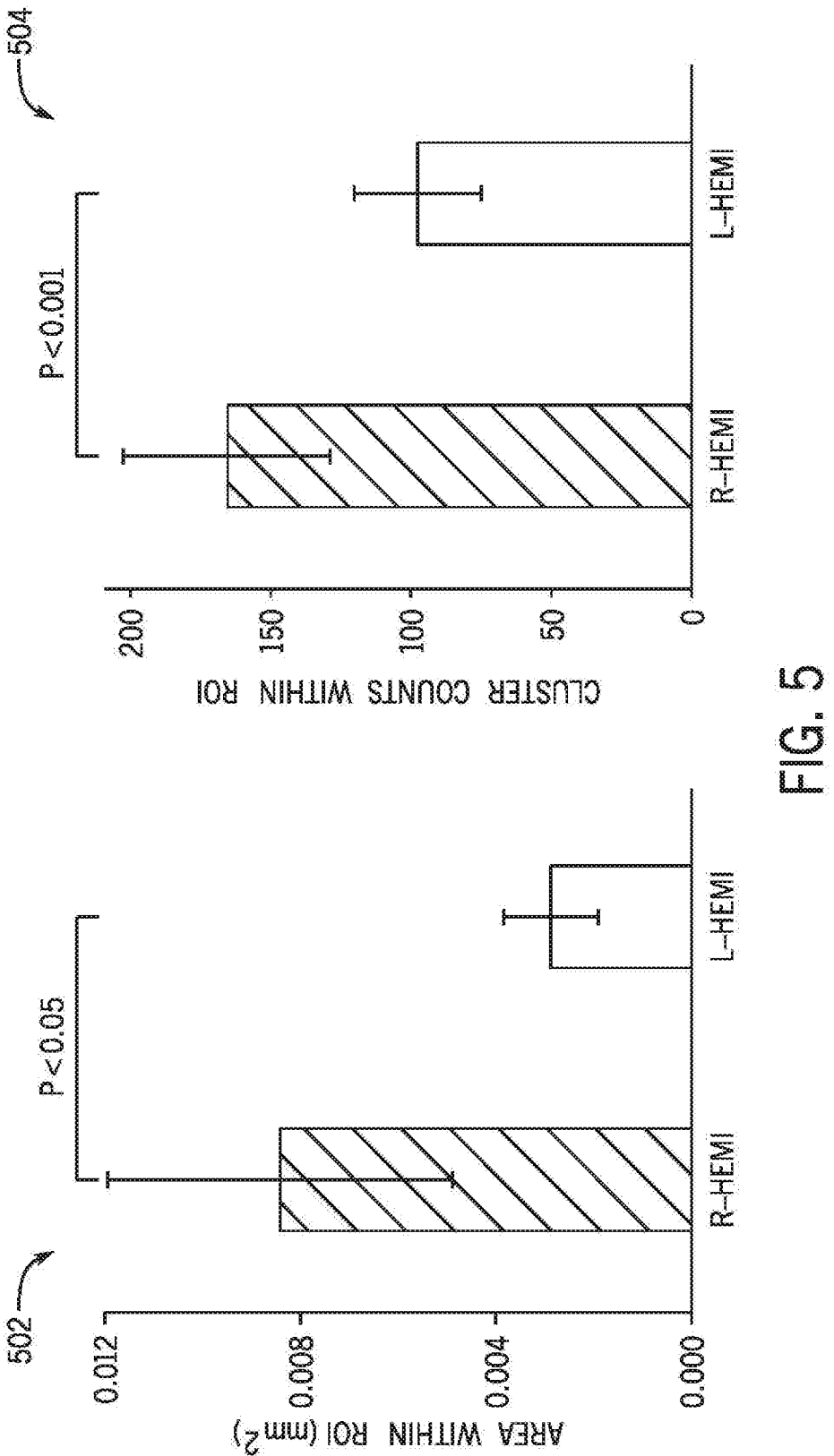
FIG. 5 shows example plots illustrating a comparison of phenytoin IHC results in accordance with an embodiment.

FUS was delivered to the brain areas in the right hemisphere at a fundamental frequency of 250 kHz in a pulsed manner (55 ms TBD, 4 Hz PRF, at 5 W/cm$^2$ I$_{sppa}$) for 35 minutes. FIG. 4 illustrates example mosaic H&E microscope images 402, example, mosaic phenytoin-stained IHC images 404 and example inverted grayscale images 406 of the phenytoin IHC in accordance with an embodiment. In this example, there was no evidence of tissue injury or hemorrhage due to sonication as shown by the example mosaic H&E images 402. In the IHC images 404, the dotted ovals 408 indicate the approximate location of the FUS sonication focus (in the right hemisphere of the brain). The sonicated brain areas (sonication focus) within the right hemisphere showed elevated levels of phenytoin (i.e., increased uptake) compared to the corresponding location in the unsonicated brain left hemisphere. This indicates that the phenytoin, unbound from the PP, was able to diffuse across the blood brain barrier to the brain parenchyma. The elevated phenytoin uptake in the brain parenchyma, is confirmed by the intensity-threshold images 406 of the corresponding brain sections (the arrows indicate the regions that exhibit the increased level of phenytoin in the brain tissue, which coincide well with the FUS focal area 408 in the IHC images 404). Based on the intensity thresholding to visualize the phenytoin uptake (60%-80% of the average brain parenchymal pixel intensity), an increased number of thresholded pixels in the sonicated right hemisphere compared to the unsonicated left hemisphere was observed in the FUS sonication focus 408;

FIG. 5 shows example plots illustrating a comparison of phenytoin IHC results in accordance with an embodiment. Graph 502 shows a comparison of the total pixel area within the thresholded range representing phenytoin-stained tissue and cells within the sonicated right hemisphere region of interest and the unsonicated left hemisphere region of interest. Graph 504 shows comparison of the total number of pixel clusters within the thresholded range representing phenytoin-stained tissue and cells within the sonicated right hemisphere region of interest and the unsonicated left hemisphere region of interest. Quantitative assessment of phenytoin uptake in the area of sonication demonstrated a significantly higher total area of pixel clusters (graph 502) within the thresholded range (representing phenytoin-stained tissue and cells) in the sonicated right hemisphere ROI ($0.0084\pm0.0164$ mm$^2$) compared to the corresponding unsonicated left hemisphere ROI ($0.0029\pm0.0045$ mm$^2$) ($p<0.05$, paired t-test, two-tailed, n=22 tissue sections across rats 'A1-A10'). There was also a significantly higher number of pixel clusters (graph 504) within the thresholded range in the right hemisphere ROI ($165.59\pm172.73$ pixel clusters) compared to the corresponding left hemisphere ROI ($97.91\pm107.17$ pixel clusters) ($p<0.001$, paired t-test, two-tailed, n=22).

Based on the evaluation of numerical simulation of the temperature change at the sonicated brain tissue, a potential temperature change was estimated as an ignorable increase of 0.007° C. at the focus during 600 sec of sonication, thereafter reached to equilibrium state between the heating by ultrasound and cooling by conduction and perfusion. The results coincided well with in vitro testing using a chamber discussed in example 1 above. The results also confirm that the effects are non-thermal, and highly likely to be associated with mechanical effect only. In this example, it is shown that applying FUS to a local brain region can unbind the phenytoin from the PP, thus increasing the local concentration of unbound phenytoin for its diffusive introduction across the blood-brain barrier, all without interrupting the blood-brain barrier, and without the injection of microbubbles.

Computer-executable instructions for unbinding of plasma protein-bound active agents according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access The present invention has been described in terms of one or more preferred embodiments, and it should be appreciated that many equivalents, alternatives, variations, and modifications, aside from those expressly stated, are possible and within the scope of the invention.

The invention claimed is:

1. An ultrasound system for use in unbinding an active agent from a plasma protein in a target site in a subject having 1) unbound active agent that is not bound to the plasma protein and 2) bound active agent comprising the active agent bound to the plasma protein, the ultrasound system comprising:

a transducer configured to generate acoustic pressure waves; and a controller coupled to the transducer and programmed to control the transducer to produce a plurality of pulsed acoustic pressure waves in the target site of the subject the plurality of pulsed acoustic pressure waves having a set of parameters including an acoustic intensity configured to 1) disrupt a plasma protein binding between the active agent and the plasma protein of the bound active agent within the target site to cause an increase in an amount of unbound active agent in the target site, 2) ensure cavitation below a predetermined cavitation threshold, and 3) maintain a temperature of the target site below a predetermined temperature threshold.

2. The ultrasound system according to claim 1, wherein the controller is programmed to control the transducer to produce a focused plurality of pulsed acoustic pressure waves.

3. The ultrasound system according to claim 1, wherein the controller is programmed to control the transducer to produce an unfocused plurality of pulsed acoustic pressure waves.

4. The ultrasound system according to claim 1, wherein the set of parameters further includes at least one of a tone burst duration, a pulse repetition frequency, and a duty cycle.

5. The ultrasound system according to claim 1, wherein the acoustic intensity of the plurality of acoustic pressure waves is selected to produce a mechanical index (MI) below a predetermined MI threshold.

6. The ultrasound system according to claim 1, wherein the target site is a region of a brain.

7. The ultrasound system according to claim 1, wherein the plurality of pulsed acoustic pressure waves comprises one or more pulses having a tone burst duration in a range of 51 to 210 ms.

8. The ultrasound system according to claim 1, wherein the plurality of pulsed acoustic pressure waves comprises one or more pulses having a duty cycle in a range of 21% to 100%.

9. The ultrasound system according to claim 6, wherein the plurality of pulsed acoustic pressure waves comprises one or more pulses having a frequency between 100 kHz and 750 kHz.

10. A method for unbinding an active agent from a plasma protein in a target site in a subject using an ultrasound system having a transducer and a controller, the target site having 1) unbound active agent that is not bound to the plasma protein and 2) bound active agent comprising the active agent bound to the plasma protein, the method comprising:

determining, using the controller, a set of parameters for a plurality of pulsed acoustic pressure waves including an acoustic intensity configured to 1) disrupt a plasma protein binding between the active agent and the plasma protein of the bound active agent within the target site to cause an increase in an amount of unbound active agent in the target site; 2) ensure cavitation below a predetermined cavitation threshold, and 3) maintain a temperature of the target site below a predetermined temperature threshold; and generating, using the transducer, the plurality of pulsed acoustic pressure waves in the target site of the subject.

11. The method according to claim 10, wherein generating the plurality of pulsed acoustic pressure waves includes generating a focused plurality of pulsed acoustic pressure waves.

12. The method according to claim 10, wherein generating the plurality of pulsed acoustic pressure waves includes generating an unfocused plurality of pulsed acoustic pressure waves.

13. The method according to claim 10, wherein determining the set of parameters includes determining a frequency of the plurality of pulsed acoustic pressures waves in a range 100 kHz to 750 kHz based on the target site.

14. The method according to claim 10, wherein determining the set of parameters includes determining the acoustic intensity of the plurality of pulsed acoustic pressures waves to produce a mechanical index (MI) below a predetermined MI threshold.

15. The method according to claim 14, wherein determining the set of parameters includes selecting a tone burst duration for at least one pulse in the plurality of pulsed acoustic pressure waves from a range 51 to 210 ms.

16. The method according to claim 15, wherein determining the set of parameters includes selecting a duty cycle for at least one pulse in the plurality of pulsed acoustic pressure waves from a range 21% to 100%.

17. The method according to claim 16, wherein determining the set of parameters includes adjusting at least one of the parameters in the set of parameters until estimated or measured thermal effects are below a predetermined threshold.

18. The method according to claim 10, wherein the target site is a region of a brain.

* * * * *